United States Patent
Toda et al.

(10) Patent No.: US 6,797,279 B2
(45) Date of Patent: Sep. 28, 2004

(54) RHODOPSEUDOMONAS CAPSULATAS STRAIN NO. FERM BP-7434 FOR USE IN HEALTH FOODS

(75) Inventors: Nobuhiro Toda, Kobe (JP); Sachio Yoshimoto, Nisinomiya (JP); Yukizo Kudo, Akita (JP)

(73) Assignee: Biochem Industrial Co., Ltd., Hyogo (JP)

(*) Notice: Subject to any disclaimer, the term of this patent is extended or adjusted under 35 U.S.C. 154(b) by 201 days.

(21) Appl. No.: 09/958,928

(22) PCT Filed: Feb. 15, 2001

(86) PCT No.: PCT/JP01/01100

§ 371 (c)(1),
(2), (4) Date: Jan. 3, 2002

(87) PCT Pub. No.: WO01/60977

PCT Pub. Date: Aug. 3, 2001

(65) Prior Publication Data

US 2003/0039637 A1 Feb. 27, 2003

(30) Foreign Application Priority Data

Feb. 17, 2000 (JP) ......................................... 2000-040218

(51) Int. Cl.⁷ ........................... A01N 63/00; A23K 1/17; A61K 47/00; C12N 1/12; C12N 1/20

(52) U.S. Cl. ....................... 424/439; 424/93.1; 424/442; 426/61; 435/252.1; 435/822

(58) Field of Search ................................ 424/93.1, 93.4, 424/439, 442; 435/252.1, 822, 243; 426/1, 61, 6

(56) References Cited

U.S. PATENT DOCUMENTS 4,467,035 A * 8/1984 Harasawa et al.
5,935,808 A   8/1999 Hirschberg et al.
6,180,099 B1 * 1/2001 Paul

FOREIGN PATENT DOCUMENTS

| JP | 47-25379 | 10/1972 |
| JP | 53-19673 | 2/1978 |
| JP | 60-36446 | 2/1985 |
| JP | 4-248982 | 9/1992 |
| JP | 7-82556 | 3/1995 |

* cited by examiner

Primary Examiner—David M. Naff
Assistant Examiner—Deborah K. Ware
(74) Attorney, Agent, or Firm—Nixon & Vanderhye, P.C.

(57) ABSTRACT

Health foods are produced containing a biomass obtained by culturing cells of a purple photosynthetic bacterium (for example, Rhodopseudomonas capsulate FERMBP-7434 strain) and optionally in a mixture with a lactic acid bacterium (for example, lactobacillus). These health foods contribute to the maintenance of human health in good conditions or regain thereof even at a small dose causing little burden.

10 Claims, 1 Drawing Sheet

RHODOPSEUDOMONAS CAPSULATAS STRAIN NO. FERM BP-7434 FOR USE IN HEALTH FOODS

TECHNICAL FIELD

The present invention relates to a red (purple) photosynthetic bacterium that is useful for maintaining or recovering health, and a healthy food prepared with same.

BACKGROUND ART

Conventionally, Japanese Un-examined Patent Application, Tokukaisho No. 47-25379 discloses that red photosynthetic bacteria can be utilized for sewage treatment. The red photosynthetic bacteria are red non-sulfur bacterium (Athiorhodaceae) and red sulfur bacterium (Thiorhodaceae).

However, the prior art does not disclose or teach that ingestion of the red photosynthetic bacteria is effective for maintaining or recovering health.

The present invention has an object to provide a strain of the red photosynthetic bacterium and the health food prepared with same, which are effective for maintaining and recovering the health.

DISCLOSURE OF INVENTION

The inventors of the present invention, as a result of intensive study on the red photosynthetic bacterium, which was incubated in various methods, in order to attain the foregoing objects, found out that the red photosynthetic bacterium, which is incubated under a specific condition, is effective for maintaining or recovering health, to accomplish the present invention.

In short, the red photosynthetic bacterium of the present invention is characterized by being *Rhodopseudomonas capsulatas* FERMBP-7434 strain, in order to attain the object.

With the above arrangement, use of FERMBP-7434 strain achieves stable production of a healthy food that is excellently effective for maintaining or recovering the health.

The healthy food of the present invention, in order to attain the foregoing objects, is characterized by including a metabolic product obtained by incubation of the photosynthetic bacterium so as to make the photosynthetic bacterium produce a viscous material.

With the above arrangement, ingestion of the metabolic product, which is obtained by incubation of the photosynthetic bacterium so as to make the photosynthetic bacterium produce a viscous material, can recover or maintain health of a person who ingests the metabolic product.

It is preferable that the photosynthetic bacterium is *Rhodopseudomonus spp*. It is more preferable that the photosynthetic bacterium is *Rhodopseudomonas capsulatas*. It is further preferable that the photosynthetic bacterium is *Rhodopseudomonas capsulatas* FERMBP-7434.

With the above arrangement, it is possible to further ensure the recovery and maintenance of the health.

For a fuller understanding of the nature and advantages of the invention, reference should be made to the ensuing detailed description taken in conjunction with the accompanying drawings.

BEST MODE FOR CARRYING OUT THE INVENTION

Figure 1:
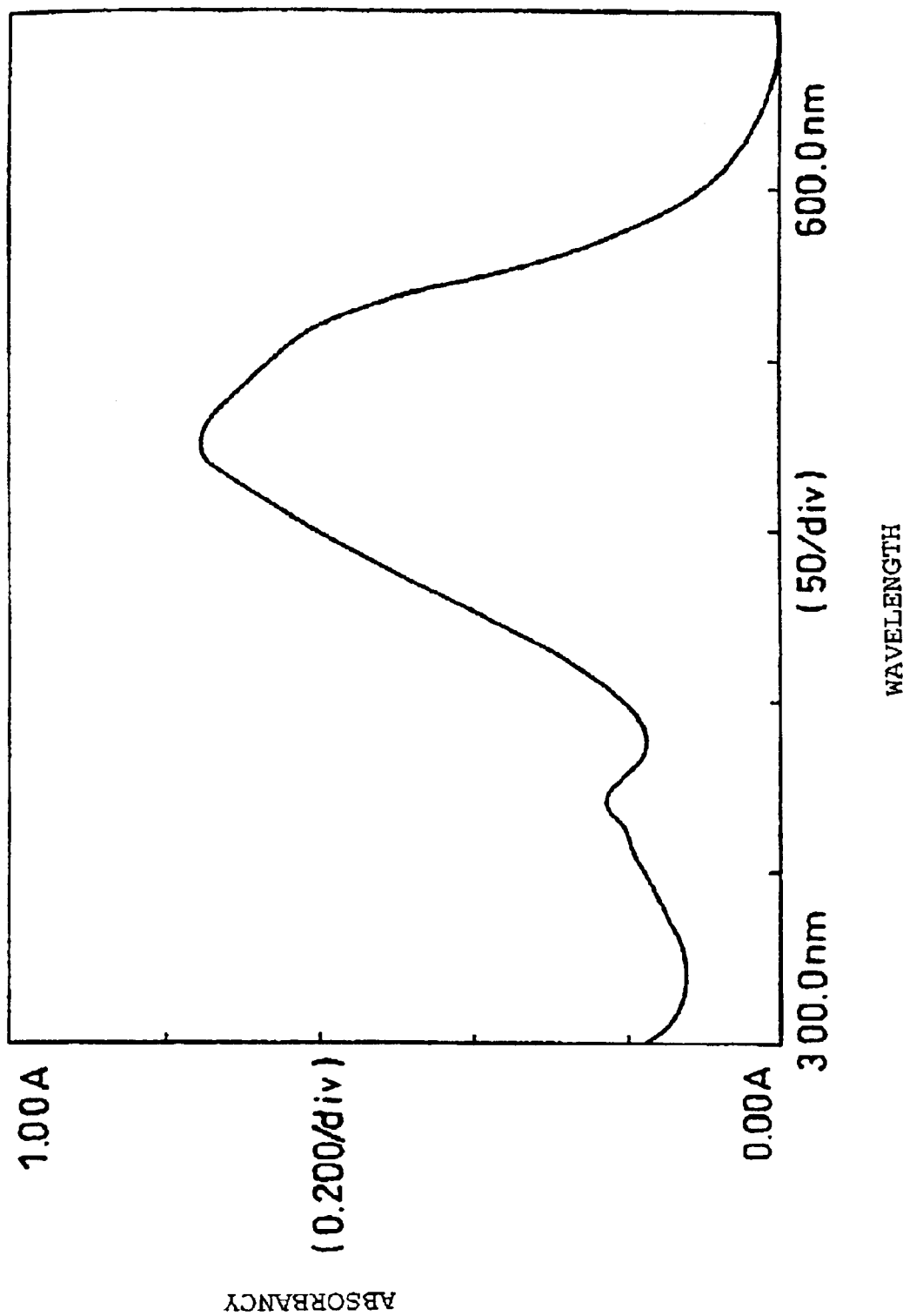
FIG. 1 is a graph illustrating absorption spectrum of an ether solution used for qualifying carotinoid materials in a sample 1. of a healthy food (TFK-RC) of the present invention.

Described below is an embodiment of the present invention.

A healthy food (TFK-RC) of the present invention contains a metabolic product of a photosynthetic bacterium that is obtained from a liquid medium prepared by incubating a bacterial solution including a photosynthetic bacterium and preferably a lactic acid bacterium so as to produce in a large quantity a viscous material from the photosynthetic bacterium. In other words, the healthy food is obtained by, for example, filtration of the liquid medium by means of centrifugation, and dehydration of a concentrated biomass, which is a residue including each biomass having the metabolic product of the photosynthetic bacterium excluding filtrate, for example by means of freeze-drying.

The thus obtained healthy food (TFK-RC), as explained later, was not toxic, and regular intake of the healthy food (TFK-RC) showed no side effect. Moreover, observed was improvement of health condition of unhealthy people who had ingested 30 mg to 360 mg, more preferably 60 mg to 240 mg of the healthy food (TFK-RC) per day for a period ranging from one week to 6 months for example, where the ingestion was in one time or preferably divided into four times (morning, noon, night and before sleep). The unhealthy people were suffering from, for example: cancer in the final stage, lymphogranuloma, severe diabetes, severe depression, severe cardiac disease, severe skin disease (including atopic dermatitis), impotency, epilepsy, hypertension (including low blood pressure), chronic constipation, chronic diarrhea, insomnia, menstrual pains, acute pneumonia, the autonomic imbalance, cerebral embolism, or polyp of the colon. The ingestion was carried out with consent of the unhealthy people and a medical doctor in charge for the unhealthy person.

Because of this, it was deduced that the healthy food (TFK-RC) improves autoimmune of the patients, and it was indicated that there was a possibility that the healthy food (TFK-RC) had efficiency for recovering health condition of the patient who ingested it, even though system of its function was unknown. Moreover, it was indicated the healthy food (TFK-RC) was effective for maintaining the health of a health person who ingested it.

The photosynthetic bacterium is, for example, a red non-sulfur bacterium, which is a red photosynthetic bacterium, *Athiorhodaceae rhodopseudomonus*, more preferably, *Rhodopseudomonas capsulatas*, or especially preferably *Rhodopseudomonas capsulatas* FERMBP-7434 strain that had been deposited at an international depository Authority for microorganisms.

The international depository authority is the National Institute of Bioscience and Human-Technology, National Institute of Advanced Industrial Science and Technology, whose address is 1-3, Higashi 1-chome, Tsukuba-shi, Ibaraki, Japan (Post Code 305-8566). The FERMBP-7434 strain was internationally deposited on Jan. 18, 2001, by requesting to transfer to depository in accordance with the terms of the Budapest Treaty, Bikokenyo No. P-17654, which had been domestically deposited at the international depository authority on Nov. 18, 1999 (original depository date). The name of the depositor is Biochem Industrial Co., Ltd. (representative: Nobuhiro TODA). Address of the depositor is 2-25-D407, 1-chome, Wadayama-dori, Hyogo-ku, Kobe-shi, Hyogo, Japan.

The lactic acid bacterium may be *Lactobacillus spp.* or *Streptococcus spp.*, for example. The *Lactobacillus spp.* may be *Lactobacillus bulgalicus* and *Lactobacillus acidophilus*, for example. The *Streptococcus spp.* may be *Streptococcus lactis* and *Streptococcus thermophilus*, for example.

Explained below is incubation condition of the bacterial solution. To begin with, as the incubation condition, the bacteria and a liquid medium (pH 6.0 to pH 8.5) including organic materials, mainly low fatty acids (at least one of a saturated fatty acid and an unsaturated fatty acid), were poured into a transparent growth tank. The incubation was carried out in the growth tank with illumination of light at 3000 lux to 10000 lux, at a temperature ranging from 23° C. to 39° C., and under an anaerobic condition. The incubation reached a stationary phase in 72 hours at latest, so that the concentrated bacteria could be obtained from the liquid medium. The liquid medium contained biotin, thiamin, and niacin as growth factors.

The incubation condition is explained below with more details. To begin with, in a mixing tank for nutrition, prepared was a base medium made of a mixture of incubation substances .$(NH_4)_2SO_4$, $KH_2PO_4$, $MgSO_4 \cdot 7H_2O$, NaCl, $NaHCO_3$, and yeast extract (including the above mentioned growth factors). In case of the incubation of the non-sulfur bacterium, low fatty acids such as acetic acid, propionic acid, and lactic acid, which were in a form of Na salt, were added into the base medium, so as to prepare the liquid medium (for example, at pH 7.0). Moreover, in case of the incubation of the red sulfur bacterium, $Na_2S \cdot 9H_2O$ was added into the base medium and adjusted by using KOH solution so as to prepare a liquid medium (at between pH 8.2 and 8.5).

Next, the liquid medium was transferred from the mixing tank for nutrition to a sealed and illuminated growth tank. Then, as the photosynthetic bacterium, for example, *Rhodopseudomonas capsulatas* FERMBP-7434 strain, which was a red non-sulfur bacterium (Athiorhodaceae), was inoculated into the sealed and illuminated growth tank.

In this case, human waste or waste liquid of shochu (Japanese distilled white liquor), in which organic acids had been generated, might be poured directly into the sealed and illuminated growth tank, instead of the liquid medium. Note that, the photosynthetic bacterium of this type also metabolizes starch, glucose, sucrose, alcohol, and other high molecular carbohydrates, thereby growing well, if various heterotrophic bacteria coexist, besides the organic acids that form the liquid medium. Because of this, it is more effective to inoculate, in the sealed and illuminated growth tank, various heterotrophic bacteria, such as the above-mentioned lactic acid bacteria, together with the photosynthetic bacterium, while adding those high molecular carbohydrates into the liquid medium. In addition, hydrogen gas generated during the incubation of the photosynthetic bacterium can be stored in a tank so as to be used as a fuel.

Consequently, the bacterial solution which had been incubated to an optimum level in the sealed and illuminated growth tank, was converted into the concentrated biomass by gathering the bacteria by means of a continuous centrifugal separator. Thereafter, the concentrated biomass was freeze-dried so as to obtain a dehydrated biomass. In the above process, when the incubated bacterial solution is transferred into the continuous centrifugal separator, it is possible to continuously obtain the identical photosynthetic bacterium, when, for example, 20% of the whole solution is always left in the growth tank so that the liquid medium prepared in the mixing tank for nutrition is added to the 20% of the liquid medium.

Note that, the reason why the sealed and illuminated growth tank was used in this method was because the photosynthetic bacterium grows optimally in the anaerobic atmosphere and under the illuminated condition (between 3000 lux and 10000 lux). Moreover, a stirring apparatus for stirring the liquid medium may be provided in the sealed and illuminated growth tank. The provision of the stirring apparatus can improve growth speed of the bacteria.

EXAMPLE

Described below is an example of the incubation of the photosynthetic bacterium. To begin with, in the mixing tank for nutrition, added into water of $1 \times 10^3$ cm$^3$ (1 liter) were:

| | |
|---|---|
| $(NH_4)_2SO_4$ | 0.3 g |
| $KH_2PO_4$ | 0.5 g |
| $MgSO_4 \cdot 7H_2O$ | 0.2 g |
| NaCl | 0.5 g |
| $NaHCO_3$ | 0.2 g |
| Yeast Extract | 0.01 g |

The respective above-listed nutrition were mixed into the water to prepare the base medium. Further, acetic acid 0.4 weight %, in the form of Na salt, and sucrose 5 weight % were added into the base medium, which was further adjusted to pH 7.0, for example, to prepare the liquid medium. Then, the liquid medium was transferred into the sealed and illuminated growth tank.

The growth tank, made of a transparent material, such as glass, in a cylinder-like shape, was illuminated by fluorescent lamps arranged in periphery of the growth tank at regular interval so as to illuminate evenly an inside of the growth tank. Meanwhile, the growth tank was provided with a stirring device that has blades of a size of a radius of the growth tank, in the growth tank. Therefore, the growth tank was capable of incubating the photosynthetic bacterium in a large quantity and with ease in the anaerobic atmosphere.

Next, a solution (bacterial concentration $10^6$ cell/cm$^3$) of *Rhodopseudomonus capsulatas* FERMBP-7434 strain was inoculated in a 20% ratio (v/v) over the total of the solution in the growth tank, then, a small quantity of a lactic acid bacterium (*Lactobacillus bulgalicus*, bacterial concentration $10^6$ cell/cm$^3$) was inoculated. The liquid medium was stirred at a rotation speed 13 times per minute at an incubation temperature 30° C. under illumination of 10000 lux. After 8 hours, the growth of the photosynthetic bacterium attained its optimum (stationary phase). Here, in the growth tank, a large quantity of the viscous material had been produced, while the photosynthetic bacterium was grown.

This liquid medium was transferred into a continuous centrifugal separator (sharp less type) so as to gather and concentrate the bacteria. The concentrated biomass was subjected to the freeze-drying, so that the biomass was obtained. The thus obtained biomass could be inoculated and obtained in a ratio of about 5 g per $1 \times 10^3$ (1 liter) of the liquid medium. As discussed later, the thus obtained biomass was quite active.

In the following, explained is a process of the freeze-drying. To begin with, the thus obtained concentrated biomass (about $10^{11}$ cell/cm$^3$) was freezed to store in a freezer, once. At the time of the freeze-drying, for example, $4 \times 10^3$ cm$^3$ (4 liter) was naturally thawed (about 12 hours), then poured and divided into 9 sucking bottles for $1.2 \times 10^3$ cm$^3$, approximately evenly (about 440 cm$^3$ each bottle)

Consequently, in a preliminary freezing tank (−45° C.), which had been filled in advance with an anti-freezing solution such as methanol, a bottom of the sucking bottles was touched with the anti-freezing solution by means of a prefreezer, while the sucking bottles were rotated, so that the concentrated biomass in the sucking bottle was freezed again so as to form a thin film along an inner wall of the sucking bottle (it was arranged that a thickness of the freezed biomass in the sucking bottle was about 8 mm, and the freezing time was about 20 minutes). The freezed concentrated biomass was stored in the freezer until the freezing of all the 9 bottles were completed.

After that, an inside of a trap of a freeze-drier was cooled down (−45° C.). After one hour since then (that is, when the cooling in the trap was completed), a vacuum pump was operated. After it was confirmed that a vacuum gauge of the vacuum pump was lowered below 26 Pa, preferably 4 to 6 Pa, the respective sucking bottles were connected with the trap. Consequently, the respective sucking bottles and the vacuum pump were linked via the trap. Then, the drying of the freezed biomass inside the respective sucking bottles was started at a room temperature (20° C. to 30° C.). The drying time, while the drying time depends on the room temperature, was about 40 hours. Note that, even though the above example used the freeze-drying method as the drying method of the concentrated biomass, it was also possible to use spray-drying as another drying method.

The thus obtained dried biomass was milled, for example, by using a crushing apparatus of a propeller-type (sample mill), where the rotation of the propellers was about 15000 rpm, so as to powder the dried biomass. Other powdering methods were, for example, a jet mill method or a ball mill method.

The powdered dried biomass may be used as the healthy food (TFK-RC) as it stands. Alternatively, the powdered dried biomass may be processed into a form of a tablet for a sake of easy ingestion. For example, a tablet-making machine of a high speed rotation type may be used for making the tablet. At the time of the tablet making process, it is possible to make the tablet without using an excipient, such as lactose, a binder, and a releasing agent such as magnesium stearate. Note that, if necessary, it may be possible to use an excipient for adjusting a dose.

In the above, explained was the example where *Rhodopseudomonas capsulatas* FERMBP-7434 strain was used. However, it may be possible to use other photosynthetic bacteria, such as Chromatium vinosum in a Thiorhodaceae family, or *Rhodospirillum Rubrum* in an Athiorhodaceae family.

Each quantification method for bacteriochlorophyll and carotenoid materials in the healthy food (TKF-RC) were carried out, based on "photosynthetic researching method" (by Sakae Kato, Kyoritsu Publishing Company: 1981).

Described below is the qualification method for the bacteriochlorophyll. To begin with, about 10 mg of a sample of the dried healthy food (TFK-RC) was taken and measured, and suspended in a physiological saline solution, 100 mm$^3$ ($\mu$l). Further, 4.9 cm$^3$ of acetone: methanol [7:2 (v/v)] was added. Then, the bacteriochlorophyll was extracted. Then, the extract was appropriately diluted Absorbancy of the diluted solution at 770 nm was measured. A concentration of the bacteriochlorophyll was calculated out by the following equation (1):

$$\text{Bacteriochlorophyll } (\mu g/cm^3) = 12.15 \, A_{770} \quad (1)$$

In the following, 5 lots of samples 1. through 5. of the bacteriochlorophyll of the present healthy food (TFK-RC), which was manufactured by the above method, were quantified, respectively. A result of the quantification is presented in Table 1.

TABLE 1

| SAMPLE NO. | SAMPLE WEIGHT (mg) | $A_{770}$ | CONTENT (mg/g) |
| --- | --- | --- | --- |
| 1. | 11.3 | 2.52 | 13.5 |
| 2. | 10.4 | 2.05 | 12.0 |
| 3. | 9.9 | 2.10 | 12.9 |
| 4. | 10.6 | 2.58 | 14.8 |
| 5. | 10.3 | 1.48 | 8.7 |

Note that, the absorbancy (770 nm) indicated by $A_{770}$ in Table 1 is a conversion value to an extracted stock solution (5 cm$^3$). The result showed that the contents (weight %) of the bacteriochlorophyll in the healthy food (TFK-RC) were between 0.2 and 3.0, preferably, between 0.6 and 1.9.

In addition, because the measurement of the absorbancy was carried out at 770 nm (red region) in the quantification of the bacteriochlorophyll, it was noted that the measurement result of the bacteriochlorophyll was not affected at all, even if the carotinoid materials were contained in the diluted solution.

Next, the quantification method of the carotinoid materials is explained. To begin with, about 10 mg of a sample of the dried healthy food was taken and measured, and was suspended in methanol, boiled to extract for one minute, and cooled down by ice. A supernatant was recovered by means of centrifugal separation. A precipitate was again suspended in the methanol. The extraction was repeated until a colorless extract was obtained, for example, for three times.

Ether in an equal quantity, and water in a double quantity with respect to the methanol extract were added into the methanol extract, and ether extraction was carried out. Then, an ether solution, which was separated out, was dehydrated. The thus obtained ether solution was measured to make 6 cm$^3$ of the ether solution. Then, absorption spectrum of the ether solution was measured.

An absorption maximum wavelength within a range from 400 to 550 nm of the absorption spectrum was determined, and absorbancy at the absorption maximum wavelength was measured. Using the absorbancy, the contents of the carotinoid materials were calculated out by the following equation (2):

$$c = D.v/1.4 \times 10^5 \quad (2)$$

c: content of carotinoid material (mol),

D: absorbancy at the absorption maximum wavelength, v: volume of ether solution (10$^3$ cm$^3$, that is, one liter), 1.4×10$^5$: an average molecular absorption coefficient of carotinoid material.

Because the maximum absorption of the carotinoid materials exists within the range from 400 to 550 nm, the absorption maximum wavelength within the range was measured from the absorption spectrum (see FIG. 1) of the ether solution. The carotinoid materials were quantified, based on the absorbancy at the absorption maximum wavelength.

Shown below in Table 2, are each quantification result of the carotinoid material as to the respective samples 1. to 5. discussed above. Moreover, absorption spectrum of the sample 1. is illustrated in FIG. 1. Absorption spectrums of the other samples 2. to 5. also showed a same pattern.

The result in Table 2 explains that contents ($\mu$mol/g) of the carotinoid materials in the healthy food (TFK-RC) were between 0.5 and 7.5, preferably between 2.4 and 4.0.

TABLE 2

| SAMPLE No. | SAMPLE WEIGHT (mg) | A.M.W (nm) | Absorbancy | CONTENT ($\mu$mol/g) |
|---|---|---|---|---|
| 1. | 9.4 | 476.5 | 0.756 | 3.45 |
| 2. | 10.8 | 476.0 | 0.868 | 3.44 |
| 3. | 11.4 | 476.0 | 0.782 | 2.94 |
| 4. | 9.6 | 476.0 | 0.666 | 2.97 |
| 5. | 10.4 | 476.0 | 0.733 | 3.02 |

ABBREVIATION: A.M.W stands for absorbancy maximum wavelength.

Moreover, according to the result in Table 1, since no absorbancy was measured above 600 nm in a visible region, it was found out that, at most, less than a quantity of a detection limit of the bacteriochlorophyll was contained in the ether extract. Therefore, as to the quantification method of the carotinoid materials, it was found out that the quantification of the carotinoid materials was not affected at all, even though the bacteriochlorophyll was contained in the healthy food (TFK-RC).

Next, as to the respective samples 1. to 5. of the healthy food, and water-washed samples of the samples 1. to 5., were respectively subjected to acid hydrolysis, and then quantified in terms of the following respective neutral monosaccharides, by means of a high performance liquid chromatographic method.

The quantification method is described below. To begin with, as to preparation of the water-washed samples, about 0.5 g of each sample was weighed and placed in a centrifugal tube. 25 cm$^3$ of water was added into the centrifugal tube and stirred, then, was subjected to ultrasonic extraction for 3 minutes, then was subjected to centrifugal separation (12,000 rpm, 5 minutes) so as to remove a supernatant. 25 cm$^3$ of water was added into a reside in the centrifugal tube and the water-washing process was processed again for two times in the same manner.

The reside, to which 25 cm$^3$ of Acetone was added in order to remove water, was stirred, then was subjected to centrifugal separation (12,000 rpm, 5 minutes) so as to remove a supernatant. After acetone remained in the centrifugal tube was volatilized under a nitrogen stream, the reside was air-dried to be the water-washed sample.

Next, explained is preparation of a test solution. To begin with, after 0.3 g to 0.6 g of each sample or 0.3 g to 0.6 g of each water-washed sample were weighed, 4 cm$^3$ of 72% sulfuric acid was added to the samples and the water-washed samples. Then, the samples were stirred for one hour at a room temperature (the water-washed samples were stirred for two hours).

Consequently, the samples and the water-washed samples were diluted with 112 cm$^3$ of water (sulfuric acid concentration: 4%), and were subjected to hydrolysis for one hour in an autoclave (121° C.). After the samples and the water-washed samples were cooled down to the room temperature, and neutralized by a sodium hydroxide solution of 30 w/v %, their volumes were adjusted to 200 cm$^3$ with water. Then, the samples and water-washed samples were filtered (No. 5B, supplied from Advantech Toyo Co., Ltd.), and further filtered with a membrane filter having a pore diameter of 0.45 $\mu$m, thereby obtaining a filtrate as the test solution.

The contents of monosaccharides (glucose, ribose, rhamnose, and fucose) were measured by the liquid chromatographic method. A result of the measurement is shown in Table 3. The measurement result indicates the contents (g) per 100 g of the healthy food (TFK-RC).

TABLE 3

| | | 1 | 2 | 3 | 4 | 5 |
|---|---|---|---|---|---|---|
| GLUCOSE | BEFORE WASHING | 5.1 | 4.6 | 4.8 | 5.0 | 5.1 |
| | AFTER WASHING | 2.1 | 2.2 | 2.2 | 2.2 | 1.7 |
| RIBOSE | BEFORE WASHING | 0.7 | 0.7 | 0.7 | 0.7 | 0.7 |
| | AFTER WASHING | 0.5 | 0.6 | 0.5 | 0.6 | 0.6 |
| RHAMNOSE | BEFORE WASHING | 2.0 | 2.0 | 2.0 | 2.0 | 2.2 |
| | AFTER WASHING | 0.9 | 0.8 | 0.8 | 0.9 | 1.0 |
| FUCOSE | BEFORE WASHING | 1.2 | 1.2 | 1.2 | 1.2 | 1.7 |
| | AFTER WASHING | 0.2 | ND | ND | ND | 0.3 |

In Table 3, ND indicates that the content was less than the detection limit (0.2 g/100 g).

According to the result in Table 3, it was found out that, in the acid hydrolyzed samples of the healthy food (TFK-RC) before washing, the contents (weight %) of glucose were in a range between 2.4 and 7.5, more preferably between 3.5 and 6.5, the contents (weight %) of ribose were in a range between 0.3 and 1.1, more preferably between 0.4 and 1.0, the contents (weight %) of rhamnose were in a range between 1.0 and 3.3, more preferably between 1.2 and 3.0, the contents (weight %) of fucose were in a range between 0.6 and 2.6, more preferably 0.8 and 2.4.

Moreover, according to the result in Table 3, it was found out that, in the acid hydrolyzed sample of the healthy food (TFK-RC) after washing, the contents (weight %) of glucose were in a range between 0.8 and 3.3, more preferably between 1.0 and 3.0, the contents (weight %) of ribose were in a range between 0.2 and 1.0, more preferably between 0.3 and 0.9, the contents (weight %) of rhamnose were in a range between 0.4 and 2.0, more preferably between 0.5 and 1.6, the contents (weight %) of fucose were less than 0.6, more preferably less than 0.5.

Next, as to the healthy food (TFK-RC) of the present invention, an acute oral toxicity test (limit test) was carried out. In short, the acute oral toxicity test (limit test) as to samples of the healthy food (TFK-RC) was carried out by using mice, in accordance with OECD (Organization for Economic Cooperation and Development) chemical substance test guide (1987).

A test group of male and female mice was subjected to single-time oral administration of 2,000 mg/kg of the sample, while a control group of them was orally given purified water, as a control solvent, one time. As a result, no abnormality or expiry of the tested animals was observed. Therefore, it was judged that an $LD_{50}$ value of the single-time oral administration as to the tested mice was more than or equal to 2,000 mg/kg for both the male and the female mice.

The test is explained below. To begin with, the sample of the healthy food (TFK-RC) was suspended in purified water to prepare 100 mg/cm$^3$ of a test solution.

The tested animal was as follows. To being with, ICR-type male and female mice of 4 week old were purchased from Japan SLC Co., Ltd. After the mice were preliminarily kept for about one week for checking their general condition was not abnormal, the mice were used for the test. The tested animals were put in cages made of polycarbonate, which respectively contained 5 of the tested animals, and were kept in a breeding room in which a room temperature was set at 23±2° C. and illumination time was set at 12 hours per day. Feed (solid feed for mice and rats; lab MR stock, made by Japan agricultural products industry Co., Ltd.) and drinking water (tap water) were freely given.

The testing method was as follows. To begin with, both the tested group and the control group had 10 of the male and the female mice, respectively. Before the administration, the tested animals were fasted for about 4 hours. After their body weight was measured, the tested group, both the males and the females, was subjected to a forcible single-time oral administration of the test solution whose dosage, a sample administration amount, was 2,000 mg/kg, by using a stomach sonde. As to the control group, 0.6 cm³ of the purified water was administered to the males, and 0.5 cm³ of the purified water was administered to the females, in the same manner.

The observation period was 14 days. Observation was carried out frequently on the day of the administration. The observation was carried out once a day from the following day. On 7 days and 14 days since the administration, the body weight was measured, and a comparison between the groups was carried out by t-inspection with a 5% level of significance. At an end of the observation period, all the tested animals were anatomized. A result of the test was as shown in Table 4. In parentheses in Table 4, shown is a number of the animals.

TABLE 4

| ADMINISTRATED GROUPS | | BEFORE AD. | AFTER AD. (DAY) | |
|---|---|---|---|---|
| | | | 7 | 14 |
| MALE | TESTED G. | 28.2 ± 0.8 (10) | 33.9 ± 1.3 (10) | 37.7 ± 2.0 (10) |
| | CONTROL G. | 28.1 ± 0.8 (10) | 33.8 ± 0.8 (10) | 36.8 ± 1.8 (10) |
| FEMALE | TESTED G. | 24.3 ± 0.6 (10) | 27.0 ± 1.2 (10) | 28.9 ± 1.4 (10) |
| | CONTROL G. | 24.0 ± 0.5 (10) | 27.4 ± 1.6 (10) | 29.3 ± 1.9 (10) |

ABBREVIATION:
AD. STANDS FOR ADMINISTRATION.
G. STANDS FOR GROUP.

In the above test, no expiry was observed for both the males and the females during the observation period. No abnormality was observed for both the males and the females during the observation period. As to the body weight measurement on 7 days and 14 days since the administration, no difference between the groups in terms of weight gain was observed as for both the males and the females, as shown in Table 4. In the anatomy after the observation period, no abnormality was found in main internal organs of all the tested animals for both the males and the females.

According to the OECD chemical substance test guide (1987), it is instructed that an intensive test for determining an $LD_{50}$ value is necessary in case expiry is observed with dosage of 2000 mg/kg.

However, in the above test result, no expiry was observed with this dosage, and no abnormality was found at the anatomy, too. Therefore, it was judged that the $LD_{50}$ value of the single-time oral administration to the tested mice was more than or equal to 2000 mg/kg for both the males and the females.

Because of this, it was proved that the healthy food (TKF-RC) of the present invention does not adversely affect a human body even in case of regular intake of the healthy food (TKF-RC).

In the following, morphological characteristics, growth conditions, and physiological characteristics of *Rhodopseudomonas capsulatas* are described.

a. Morphological Characteristics

*Rhodopseudomonas capsulatas* has a flagellum and is quite motile. Generally, they are short bacilli (width 0.5µx length 1.0µ), while some are long bacilli (width 0.5µ to 0.7µ×length 6.0µ), depending on a type of liquid media and incubation periods. In other words, they shows polymorphism.

b. Growth Conditions

The growth result (anaerobic and under illumination) on various media are described below.

| | | | |
|---|---|---|---|
| Meat Extract | + | Lactic Acid | ++ |
| Peptone Water | +++ | Succinic Acid | + |
| Potato Medium | – | Malic Acid | + |
| Thiosulfate | – | Butyric Acid | ++ |
| Alanine | + | Crotonic Acid | + |
| Leucine | – | Pyruvic Acid | ++ |
| Asparagine | + | Ethanol | + |
| Aspartic Acid | – | Mannitol | – |
| Glutamic Acid | + | Sorbitol | – |
| Tartaric Acid | – | Mannose | – |
| Citric Acid | – | Fructose | – |
| Glutaric Acid | + | Glycerol | – |
| Acetic Acid | + | | |
| Propionic Acid | +++ | | |

(All the substrates were used in 0.2 weight % concentration.)
Note:
+++ Growth was good.
+ Growth was possible.
– Growth was impossible.

c. Physiological Characteristics

1) Optimal Growth Condition
    pH 7.2, temperature 27° C.,
    anaerobic illumination 10,000 lux
2) Condition which allows the growth
    pH 6.0 to pH 8.5, temperature 23° C. to 39° C., aerobic to anaerobic dark condition to illumination condition
3) Gram Staining Characteristics
    Negative
4) Anti-acid Characteristics
    Positive
5) Indole production
    Negative
6) Hydrogen Sulfide Production
    Negative
7) Ability for Nitrogen Gas Fixation
    Positive
8) It also carries out denitrification in a nitrate medium, in which nitric acid is reduced and converted to a gas of $N_2$, on contrary to the nitrogen fixation.
9) Catalase Production
    Positive
10) Gelatine Liquefaction
    Negative
11) Starch Hydrolysis
    Negative
12) Ability to oxidize Methylene Blue of a reduction type, Methyl (or Benzyl) Biorodien pigment of a reduction type
    Positive
13) It requires Biotin, Thiamin, and Nicotinic Acid as growth factors.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

A red photosynthetic bacterium of the present invention is, as discussed above, *Rhodopseudomonas capsulatas* FERMBP-7434 strain.

Therefore, because the red photosynthetic bacterium is FERMBP-7434 strain, the above arrangement can provide stably a healthy food that has an excellent function for maintaining and recovering health.

The healthy food of the present invention is arranged to have a metabolic product obtained by incubating the photosynthetic bacterium so that a viscous material is produced from the photosynthetic bacterium.

Therefore, because the healthy food has the metabolic product obtained by incubating the photosynthetic bacterium so that a viscous material is produced from the photosynthetic bacterium, the above arrangement can provide the healthy food, administration of which can maintain or recover the health.

What is claimed is:

1. A biologically pure culture of a photosynthetic bacterium *Rhodopseudomonas capsulatas* strain FERM BP-7434.

2. A healthy food, comprising:
   biomass obtained by incubating the photosynthetic bacterium as set forth in claim 1, said biomass containing cells of said bacterium and a viscous material produced by said bacterium; wherein
   said biomass has glucose contents ranging from 2.4 to 7.5 (weight %), ribose contents ranging from 0.3 to 1.1 (weight %), rhamnose contents ranging from 1.0 to 3.3 (weight %), and fucose contents ranging from 0.6 to 2.6 (weight %) after acid hydrolysis and before water washing; and
   said biomass has glucose contents ranging from 0.8 to 3.3 (weight %), ribose contents ranging from 0.2 to 1.0 (weight %), rhamnose contents ranging from 0.4 to 2.0 (weight %), and fucose contents less than 0.6 (weight %) after acid hydrolysis and after water washing.

3. The healthy food as set forth in claim 2, wherein a lactic acid bacterium is incubated together with the photosynthetic bacterium.

4. The healthy food as set forth in claim 2, further comprising:
   bacteriochlorophyll in a range between 0.2 and 3.0 (weight %).

5. The healthy food as set forth in claim 2, further comprising:
   carotinoid materials in a range between 0.5 and 7.5 ($\mu$mol/g).

6. The healthy food as set forth in claim 2, wherein
   said biomass has glucose contents ranging from 3.5 to 6.5 (weight %), ribose contents ranging from 0.4 to 1.0 (weight %), rhamnose contents ranging from 1.2 to 3.0 (weight %), and fucose contents ranging from 0.8 to 2.4 (weight %) after acid hydrolysis and before water washing.

7. The healthy food as set forth in claim 2, wherein
   said biomass has glucose contents ranging from 1.0 to 3.0 (weight %), ribose contents ranging from 0.3 to 0.9 (weight %), rhamnose contents ranging from 0.5 to 1.6 (weight %), and fucose contents of less than 0.5 (weight %) after acid hydrolysis and after water washing.

8. A mixed culture comprising photosynthetic bacteria *Rhodopseudomonas capsulatas* strain FERM BP-7434 as set forth in claim 1 and lactic bacteria.

9. The culture as set forth in claim 8, wherein the lactic bacteria is a *Lactobacillus spp.* or a *Streptococcus spp.*

10. A method of producing a healthy food comprising:
    (a) incubating at least photosynthetic bacteria of *Rhodopseudomonas capsulatas* strain FER BP-7434 as set forth in claim 1 under conditions to produce a biomass containing cells of said bacteria and a viscous material produced by said bacteria and
    (b) processing the biomass to obtain said healthy food.

* * * * *